US012724018B2

(12) United States Patent
Lee et al.

(10) Patent No.: US 12,724,018 B2
(45) Date of Patent: Sep. 1, 2026

(54) EARLY FIRE DETECTION SYSTEM FOR AN ESS BATTERY MODULE

(71) Applicant: ALLLITELIFE CO., LTD., Anyang-si (KR)

(72) Inventors: Byung Kwon Lee, Seoul (KR); Hong Sun Ryou, Yongin-si (KR); Young Man Lee, Anyang-si (KR)

(73) Assignee: ALLLITELIFE CO., LTD., Anyang-si (KR)

( * ) Notice: Subject to any disclaimer, the term of this patent is extended or adjusted under 35 U.S.C. 154(b) by 592 days.

(21) Appl. No.: 18/317,166

(22) Filed: May 15, 2023

(65) Prior Publication Data

US 2024/0175855 A1 May 30, 2024

(30) Foreign Application Priority Data

Nov. 29, 2022 (KR) ........................ 10-2022-0163200

(51) Int. Cl.
*G01N 33/00* (2006.01)
*G01N 1/24* (2006.01)

(52) U.S. Cl.
CPC ........... *G01N 33/0063* (2013.01); *G01N 1/24* (2013.01)

(58) Field of Classification Search
CPC .......... A62C 3/16; G01N 1/2226; G01N 1/24; G01N 33/0063; H01M 10/425; H01M 10/48; H01M 10/486; H01M 10/63; H01M 2010/4271; H01M 2010/4278; H01M 50/383; G08B 17/06; G08B 17/10
See application file for complete search history.

(56) References Cited

U.S. PATENT DOCUMENTS

2022/0149449 A1* 5/2022 Kim .................... H01M 10/486
2022/0366770 A1* 11/2022 Wang ........................ B03C 3/12

FOREIGN PATENT DOCUMENTS

| | | | | |
|---|---|---|---|---|
| CN | 110667435 A * | 1/2020 | ............ G08B 17/06 |
| KR | 10-1531656 B1 | 6/2015 | |
| KR | 10-1544383 B1 | 8/2015 | |
| KR | 10-1630783 B1 | 6/2016 | |
| KR | 10-1672899 B1 | 11/2016 | |
| WO | WO-2020019578 A1 * | 1/2020 | ............ G08B 17/10 |

* cited by examiner

*Primary Examiner* — Kristina M Deherrera
*Assistant Examiner* — Gedeon M Kidanu
(74) *Attorney, Agent, or Firm* — NKL Law; Jae Youn Kim

(57) ABSTRACT

Provided is a system for early detection of fire in an ESS battery module including: an air suction-type detector that is fitted to the exterior of the ESS and detects fire by introducing gas inside the ESS battery module; a suction line, of which one end is connected to the ESS battery module, sucks gas inside the ESS battery module in real time and introducing the gas into the air suction-type fire detector; a suction pump that is fitted to one side of the suction line and supplies power for drawing air from inside the ESS battery module into the suction line; and a multiple sensing unit that is fitted to one side of the suction line and senses a temperature of the gas introduced through the suction line, as well as any generated gas.

9 Claims, 7 Drawing Sheets

EARLY FIRE DETECTION SYSTEM FOR AN ESS BATTERY MODULE

CROSS-REFERENCE TO RELATED APPLICATIONS

This application claims priority to and the benefit of Korea Patent Application No. 10-2022-0163200 filed in the Korean Intellectual Property Office on Nov. 29, 2022, the contents of which are incorporated herein by reference in their entirety.

BACKGROUND

Technical Field

The present disclosure relates to a system for early detection of thermal runaway and a fire by monitoring a sign of thermal runaway of a battery in an energy storage system (hereinafter, referred to as ESS). In particular, in respect to fire detection of a battery in an ESS through an air suction-type detector, the present disclosure relates to an early fire detection system by monitoring changes in temperatures, pressures and flow rates as well as gases generated from signs of thermal runaway, and to a detection method thereof and a program therefor.

Related Art

An interior environment with a closed chamber such as an ESS has a rapid and dry air flow by an air conditioner. However, a fire spreads rapidly due to the aforementioned environment of the ESS under the fire situation. Thus, it is supposed to detect a fire in the early stage to minimize damage and losses of the ESS.

FIGS. 1A and 1B show examples in which an air suction-type fire detection system is applied. FIG. 2 is a mimetic diagram of an air suction-type fire detection system 1. As shown in FIG. 2, in general, an air suction-type fire detector 10 is used in an ESS 2.

It is seen that such a prior air suction-type fire detection system 1 is configured to include a suction line 20 that is fitted to the inside of the ESS 2, a connection line that links the suction line 20 and a fire detector 10, and a suction pump that is furnished on one side of the connection line, this supplying power for drawing air from inside the ESS 2 into the suction line.

Further, the fire detector 10 is configured to determine whether a fire have occurred by detecting smoke from the air inside a warehouse 23, which is drawn through the suction line 20, in real time.

In general, ESS (Energy Storage System) is a device that makes electric energy stored therein reusable when needed. The ESS stores electric energy in a battery system, and then uses the stored electric energy when needed, enhancing usability of new renewable energy and promoting stabilization of an energy supply system. This is applicable to various fields for supplying electric energy, used as an environment friendly and efficient energy source.

One type of rechargeable batteries is a lithium-ion battery that has a multilayered structure including a positive electrode activated by various mixed oxides or peridot, a negative electrode activated by a special carbon, and a separation membrane completely immersed in an organic electrolyte. The common battery is housed in an enclosure, forming a battery module.

During normal operation, electric energy is converted into chemical energy and then stored during the recharging process. In more detail, during the recharging process, lithium at the positive electrode is ionized and lithium ions migrate through layers to the negative electrode, whereas during the discharging process, the ions migrate back to the positive electrode and return to their original compound state. Several lithium-ion battery modules are mounted in a rack assembly to form a battery pack.

In a certain extremal case such as over voltage, over current or over heat, a state of "self-heating" may occur in the lithium-ion battery, this causes the battery to enter a state of "thermal runaway". The term "self-heating" refers to a state where a temperature inside a battery cell increases due to the electro-chemical reactions occurring within it. The thermal runaway occurs when the temperature inside the battery cell increases to a level in which a chemical reaction takes place and a flammable gas is emitted.

When there is sufficient oxygen in an enclosure housing a battery cell, the flammable gas ignites and a great amount of energy may be emitted.

The thermal runaway in a single battery module can cause significant and extensive damage. Once the thermal runaway occurs, a small amount of oxygen is generated, which results in the inside temperature increasing higher than 800° C. When the aforementioned situations occur simultaneously, a fire may be break out inside the battery module, excessive gas may be generated, and then the enclosure surrounding the lithium ion cell may be destroyed. The fire rapidly consumes the oxygen generated inside the cell and continues to consume oxygen around it.

The excessive gas generated in the battery module may increase beyond the safe limit of the internal pressure, causing destruction such as the enclosure being destroyed. Thus, a technique is known for providing an enclosure with a pressure relieving unit or a blasting unit, which allows the excessive gas to escape from the module. However, when this gas is mixed with ambient air and a resulting mixture exists between the lower limit of ignition and the upper limit of ignition, the mixture may spontaneously ignite and potentially cause an explosion. These potential problems become worse in a certain battery system that uses a blower to make the heat generated during the operation flow over the battery module. When thermal runaway occurs in this system, the blower can cause mixing of the excessive gas and surrounding air, thereby increasing the risk of a potentially dangerous mixture.

The term 'secondary battery' refers to a rechargeable battery, as opposed to a primary battery which cannot be recharged. Secondary batteries are used as power sources for small electronic devices such as cell phones, PDAs, laptops, energy storage systems (ESS), electric vehicles (EVs), and hybrid electric vehicles (HEVs).

Commonly used types of secondary batteries include lithium-ion batteries, lithium-polymer batteries, nickel-cadmium batteries, nickel-hydrogen batteries, nickel-zinc batteries, and others. The operating voltage of a single secondary battery cell typically ranges from approximately 25V to 42V.

Accordingly, when an output voltage higher than this and an energy capacity are required, a battery module is formed by series connection of a plurality of battery cells, alternatively forming a battery pack by series connection or parallel connection of at least two battery modules mentioned above and adding other components. For example, the battery module refers to a device in which multiple secondary batteries are connected in series or parallel, and the battery pack refers to a component in which battery modules are connected in series or parallel to increase the capacity and output thereof. The number of battery cells included in the battery pack may be set variously depending on the required output voltage or recharging and discharging capacity.

As the battery cell inside the battery module repeats recharging and discharging processes, this may cause the phenomenon of battery swelling, that is, the battery cell swells up.

The swelling phenomenon may be generated by various causes such as over-charging or discharging, a short circuit, leaving at a high temperature and the like, and this may result in shortening the lifespan of the secondary battery, decreasing the capacity and performance thereof and safety accidents such as ignition and explosion.

When typically stacking battery cells in the battery module, the battery cells are arranged spaced apart from each other at a regular interval. Alternatively, compressed pads for supporting the battery cell during the swelling of the battery are arranged in-between the battery cells.

When a problem such as a short circuit in some battery cells inside the battery module, the temperature continuously increases and the temperature of the battery cell exceeds a critical temperature, causing thermal runaway.

Flames occurred by the thermal runaway in some of batteries inside the battery module sharply increase the temperature of adjacent battery cells, whereby propagating the thermal runaway over those adjacent battery cells.

After all, if failing to handle the thermal runaway occurring in some of those battery cells quickly, this causes safety accidents such as the ignition or explosion of the battery module or battery pack that is a battery unit with a larger capacity.

In general, the battery module include a housing that stores and packs battery cells therein and protects these battery cells from external shocks. The housing is typically made of a thick steel sheet to ensure the safe protection of the battery cells from external shocks. However, there is a problem that this cannot prevent rapid propagation of the thermal runaway occurring in some of battery cells to other battery cells.

RELATED ART DOCUMENT

Patent Document (Patent Document 1) Korean Patent No. 1672899
(Patent Document 2) Korean Patent No. 1630783
(Patent Document 3) Korean Patent No. 1544383
(Patent Document 4) Korean Patent No. 1531656

SUMMARY

Technical Problem

Therefore, the present disclosure is contrived to overcome conventional problems as described above. According to an embodiment of the present disclosure, the aim is to provide an early fire detection system for an ESS battery module, a detection method thereof and a program therefor. This is achieved by primarily sensing the signs through a suction line of an air suction-type detector, using a detection sensor in a multiple sensing unit and secondarily monitoring smoke in the air suction-type detector, when signs (CO, $CO_2$, VOCs) of thermal runaway are generated in an ESS battery.

Further, according to an embodiment of the present disclosure, the aim is to provide an early fire detection system for ESS battery module. This is achieved by monitoring event situations and changes in the environment situation through monitoring and controlling changes in temperatures, pressures and flow rates of air currents introduced through a suction line of an air suction-type detector.

According to an embodiment of the present disclosure, the aim is to provide an early fire detection system for ESS battery module and a detection method thereof. In respect to the air suction-type fire detector for preventing fire in an ESS room, this is to achieved by installing a multiple sensing unit on one side of a suction line and monitoring sings of thermal runaway before it occurs in the ESS.

According to an embodiment of the present disclosure, the aim is to provide an early fire detection system for ESS battery module and a detection method thereof. This is achieved by monitoring the gas generated during the thermal runaway using the multiple sensing unit and monitoring signs of thermal runaway before it occurs in the ESS.

Meanwhile, technical objects to be achieved in the present invention are not limited to the aforementioned technical objects, and other technical objects, which are not mentioned above, will be apparently understood to a person having ordinary skill in the art from the following description.

Technical Solution

An aspect of the present disclosure may be achieved by providing a system for early detection of fire in an ESS battery module. The early fire detection system for an ESS battery module includes: an air suction-type detector that is fitted to the exterior of the ESS and detects fire by introducing gas inside the ESS battery module; a suction line of which one end is connected to the ESS battery module, sucks gas inside the ESS battery module in real time and introducing the gas into the air suction-type fire detector; a suction pump that is fitted to one side of the suction line and supplies power for drawing air from inside the ESS battery module into the suction line; and a multiple sensing unit that is fitted to one side of the suction line and senses a temperature of the gas introduced through the suction line, as well as any generated gas.

Further, the generated gas is one generated during thermal runaway.

Further, the multiple sensing unit includes: a temperature sensor that measures a temperature of gas introduced through a suction line, in real time; a humidity sensor that measures a humidity in real time; and a gas sensor that measures a concentration of the generated gas.

Further, the gas sensor includes a CO sensor, a $CO_2$ sensor and a VOCs sensor.

Further, the early fire detection system for an ESS battery module further includes a monitoring unit that receives measurements of concentration temperature and humidity of the generated gas from the multiple sensing unit, primarily monitoring battery thermal runaway and secondary monitoring based on a smoke concentration measured in the air suction-type detector.

Further, the monitoring unit further includes: a database that stores preset values for temperature, CO concentration, $CO_2$ concentration and VOCs concentration; and a determination portion that determines a state when each value measured in the temperature sensor, the CO sensor, the $CO_2$ sensor and the VOCs sensor respectively exceeds the respective preset values for temperature, CO concentration, $CO_2$ concentration and VOCs concentration as a sign of thermal runaway.

Further, a preset smoke concentration value is stored in the database. The determination portion determines a fire outbreak stage when a pre-thermal runaway state is identified and a smoke concentration measured in the air suction-type detector exceeds the preset smoke concentration value.

Further, the database stores a simulation of when battery thermal runaway occurs, or graphs showing changes in temperature, CO concentration, $CO_2$ concentration, VOCs concentration and smoke concentration.

Further, the determination portion determines a pre-thermal runaway state or a thermal runaway state by matching at least one selected from: the temperature change graph stored in the database and a temperature change graph measured in the multiple sensing unit; the CO concentration change graph stored in the database and a CO concentration change graph measured in the multiple sensing unit; the $CO_2$ concentration change graph stored in the database and a $CO_2$ concentration change graph measured in the multiple sensing unit; and the VOCs concentration change graph stored in the database and a VOCs concentration change graph measured in the multiple sensing unit.

Further, the determination portion determines whether or not fire have occurred and identifies a state of fire by matching the smoke concentration graph stored in the database with a smoke concentration change graph measured in the air suction-type detector.

Further, the monitoring unit further includes a display portion that displays the measured graphs showing changes in temperature, CO concentration, $CO_2$ concentration and smoke concentration.

Further, the early fire detection system for an ESS battery module further includes an alarm unit that transmits alarm data when determination portion identifies a state of pre-thermal runaway, thermal runaway or fire.

Further, the early fire detection system for an ESS battery module further includes a communication module that transmits the determination data to a preset user terminal.

Advantageous Effects

According to an early fire detection system for an ESS battery module, a detection method thereof and a program therefor, it is capable of primarily sensing the signs through a suction line of an air suction-type detector, using a detection sensor in a multiple sensing unit and secondarily monitoring smoke in the air suction-type detector, when signs (CO, $CO_2$, VOCs) of thermal runaway are generated in an ESS battery.

Further, according to an embodiment of the present disclosure, the aim is to provide an early fire detection system for ESS battery module, it is capable of monitoring event situations and changes in the environment situation through monitoring and controlling changes in temperatures, pressures and flow rates of air currents introduced through a suction line of an air suction-type detector.

According to an embodiment of the present disclosure, the aim is to provide an early fire detection system for ESS battery module, in respect to the air suction-type fire detector for preventing fire in an ESS room, it is capable of installing a multiple sensing unit on one side of a suction line and monitoring sings of thermal runaway before it occurs in the ESS.

According to an embodiment of the present disclosure, the aim is to provide an early fire detection system for ESS battery module, it is capable of monitoring the gas generated during the thermal runaway using the multiple sensing unit and monitoring signs of thermal runaway before it occurs in the ESS.

Meanwhile, advantageous effects to be obtained in the present disclosure are not limited to the aforementioned effects, and other effects, which are not mentioned above, will be apparently understood to a person having ordinary skill in the art from the following description.

BRIEF DESCRIPTION OF THE DRAWINGS

The accompanying drawings of this specification exemplify a preferred embodiment of the present disclosure, the spirit of the present disclosure will be more clearly understood from the following detailed description taken in conjunction with the accompanying drawings, and thus it will be understood that the present disclosure is not limited to only contents illustrated in the accompanying drawings.

DETAILED DESCRIPTION

Figure 1A:
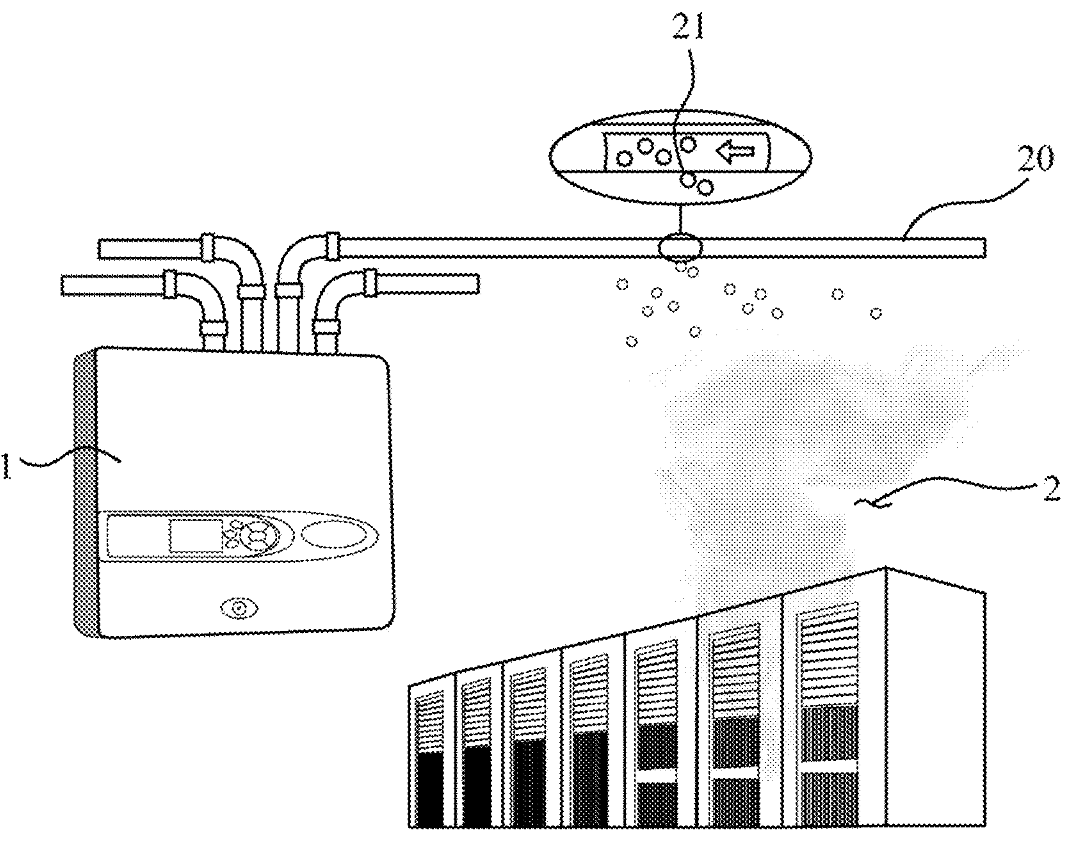
FIG. 1A and FIG. 1B show examples in which an air suction-type fire detection system is applied to an ESS room.
Figure 1B:
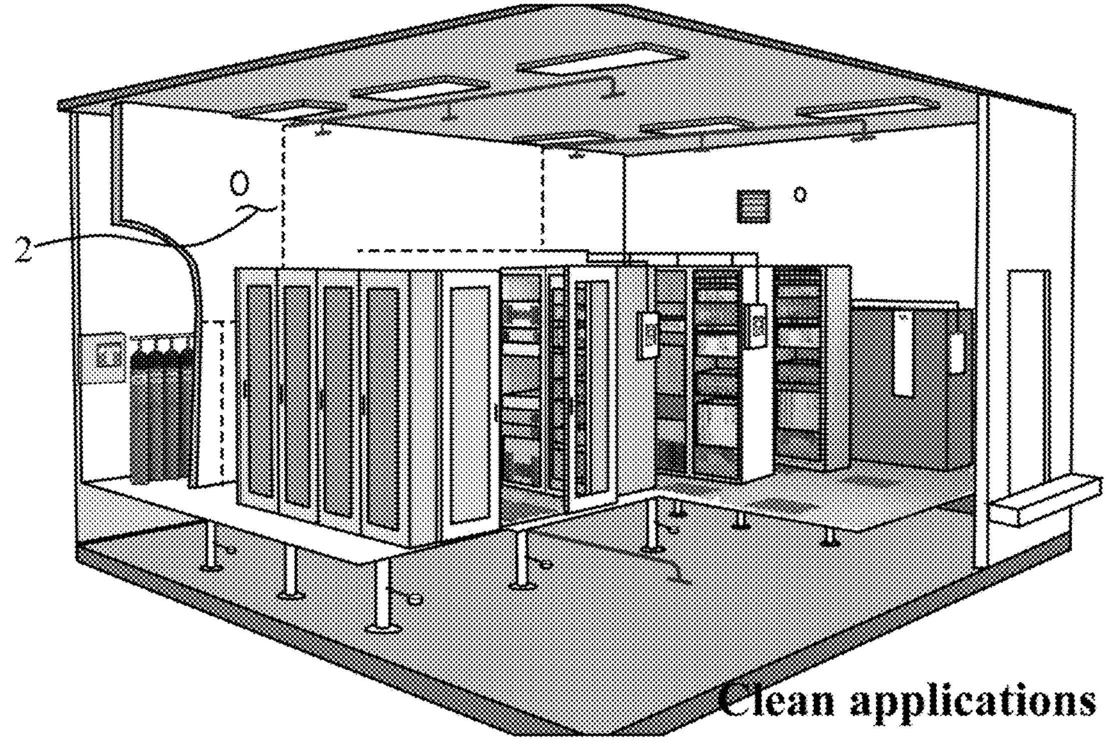
Figure 2:
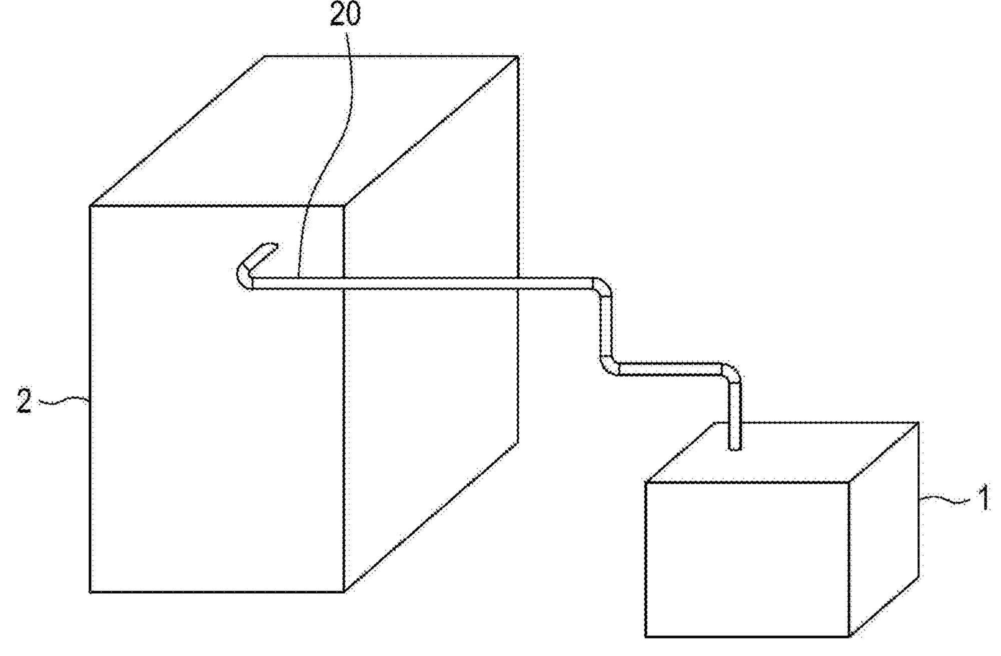
FIG. 2 is a mimetic diagram of an air suction-type fire detection system

Hereinafter, the aforementioned aims, other aims, features and advantageous effects of the present disclosure will be understood easily referring to preferable embodiments related to the accompanying drawings. However, the present disclosure is not limited to embodiments described in this specification, and may be embodied into other forms. Preferably, the embodiments in this specification are provided in order to allow disclosed contents to be exhaustive and to communicate the concept of the present disclosure to those skilled in the art.

In this specification, when a certain element is placed on another element, this means that it may be formed directly thereon or that the third element may be interposed between them. Further, in the drawings, the thickness of an element may be overstated in order to explain the technical content thereof efficiently.

The embodiments described in this specification will explained with reference to a cross-sectional view and/or a plane view. In the drawings, the thickness of a film and a region may be overstated in order to explain the technical content thereof efficiently. Accordingly, the form of exemplary drawings for a fabrication method and/or an allowable error et cetera may be modified. Thus, the embodiments according to the present disclosure are not limited to specific forms illustrated herein, but may include variations in the form resulting from the fabrication method. For example, the region illustrated with perpendicular lines may have a form to be rounded or with a predetermined curvature. Thus, regions exemplified in the drawings have attributes, and shapes thereof exemplify specific forms rather than limiting the scope of the present disclosure. In the various embodiments of this specification, terms such as 'first' and 'second' et cetera are used to describe various elements, but these elements should not be limited to such terms. These terms are merely used to distinguish one element from others. The embodiments explained and exemplified herein may include complementary embodiments thereto.

The terms used in this specification is to explain the embodiments rather than limiting the present disclosure. In this specification, the singular expression includes the plural expression unless specifically stated otherwise. The terms, such as 'comprise" and/or "comprising" do not preclude the potential existences of one or more elements.

When describing the following specific embodiments, various kinds of specific contents are made up to explain the present disclosure in detail and to help understanding thereof. However, it will be apparent for those who have knowledge to the extent of understanding the present disclosure that the present disclosure can be used without any of these specific contents. In a certain case when describing the present disclosure, the content that is commonly known to the public but is largely irrelevant to the present disclosure is not described in order to avoid confusion.

Hereinafter, the configuration, functions and detection method of an early fire detection system for an ESS battery module according to an embodiment of the present disclosure will be described.

Figure 3:
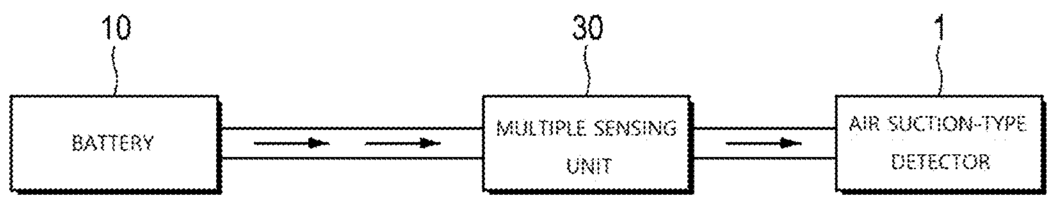
FIG. 3 is a schematic diagram of an early fire detection system for an ESS battery module according to an embodiment of the present disclosure.
Figure 4:
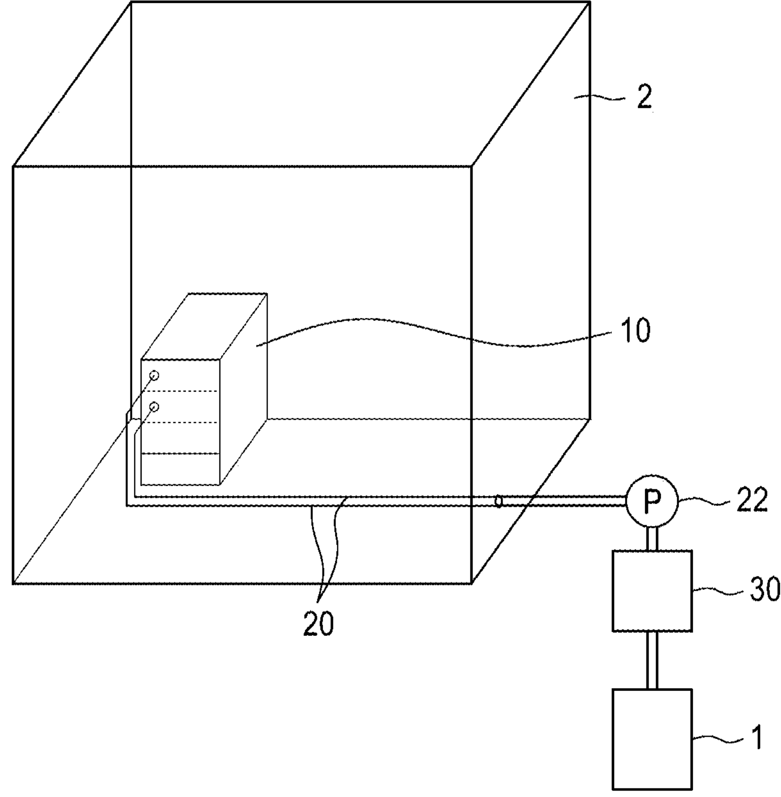
FIG. 4 is a schematic diagram of installation of an early fire detection system for an ESS battery module according to an embodiment of the present disclosure.

FIG. 3 is a schematic diagram of an early fire detection system for an ESS battery module according to an embodiment of the present disclosure. FIG. 4 is a schematic diagram of installation of an early fire detection system for an ESS battery module according to an embodiment of the present disclosure.

An early fire detection system for an ESS battery module 100 is a system capable of early detecting fire and thermal runaway of a battery module 10 inside an ESS 2, including an air suction-type detector 1, a suction line 20, a suction pump 22, a multiple sensing unit 30, etc.

An air suction-type detector 1 is fitted to the exterior of an ESS 2 and detects fire by introducing the gas inside the ESS battery module 10.

As shown in FIG. 4, the suction line 20 of which one end is connected to the ESS battery module 10 and of which another end is connected to the air suction-type detector 1 sucks gas in the ESS battery module 10 in real time and introduces the gas to the air suction-type detector 1. The suction pump 22 is installed on one side of the suction line 20 and supplies power for drawing air from inside the ESS battery module 10 into the suction line 20.

The multiple sensing unit 30 is installed on one side of the suction line 20 and detects a temperature of the gas introduced through the suction line 20, as well as a concentration of any generated gas in real time.

Therefore, according to an embodiment of the present disclosure, when signs (CO, $CO_2$, VOCs) of thermal runaway are generated in the ESS battery module 10, the early fire detection system for an ESS battery module 100 is capable of primarily sensing the sign through the suction line 20 of the air suction-type detector, using a detection sensor in the multiple sensing unit 30 and secondarily monitoring smoke in the air suction-type detector 1.

Hereinafter, the configuration and function of an early fire detection system for an ESS battery module according to an embodiment of the present disclosure will be described in more detailed.

Figure 5:
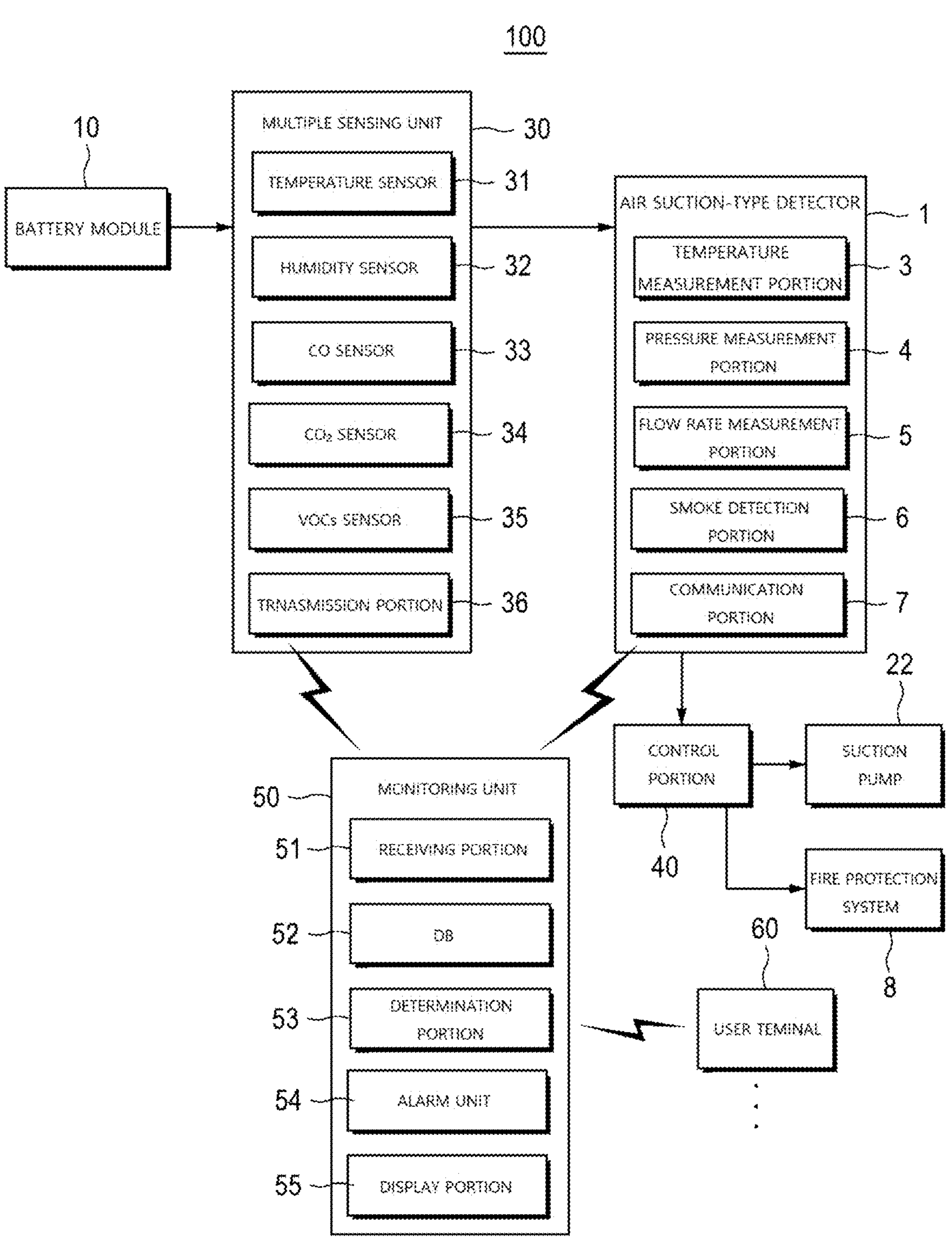
FIG. 5 is a block diagram of the whole of an early fire detection system for an ESS battery module according to an embodiment of the present disclosure.

FIG. 5 is a block diagram of the whole of an early fire detection system for an ESS battery module according to an embodiment of the present disclosure.

Figure 6:
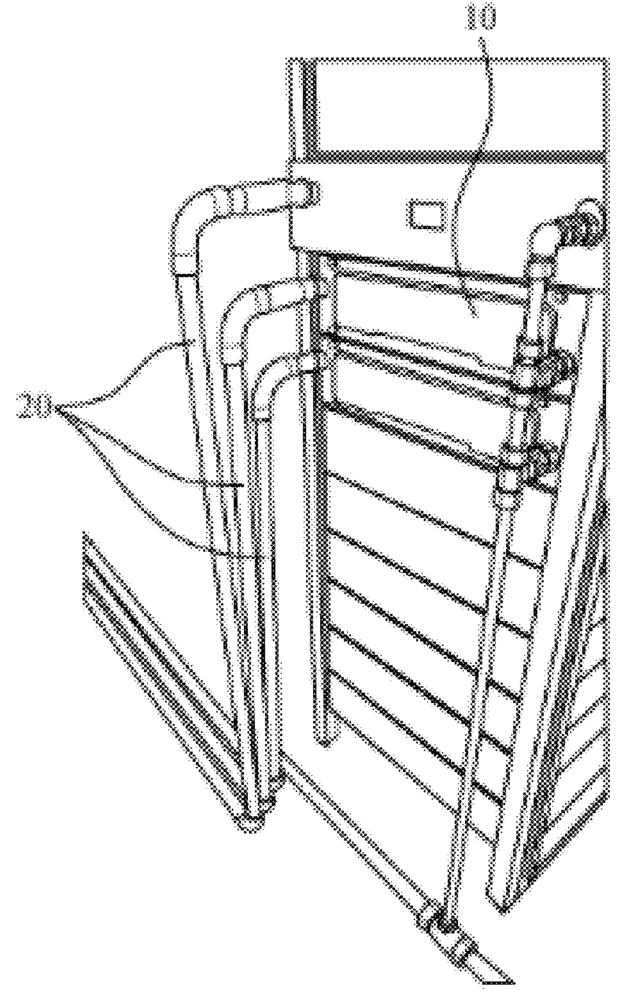
FIG. 6 is a photo showing a battery module connected with a suction hole inside ESS.
Figure 7:
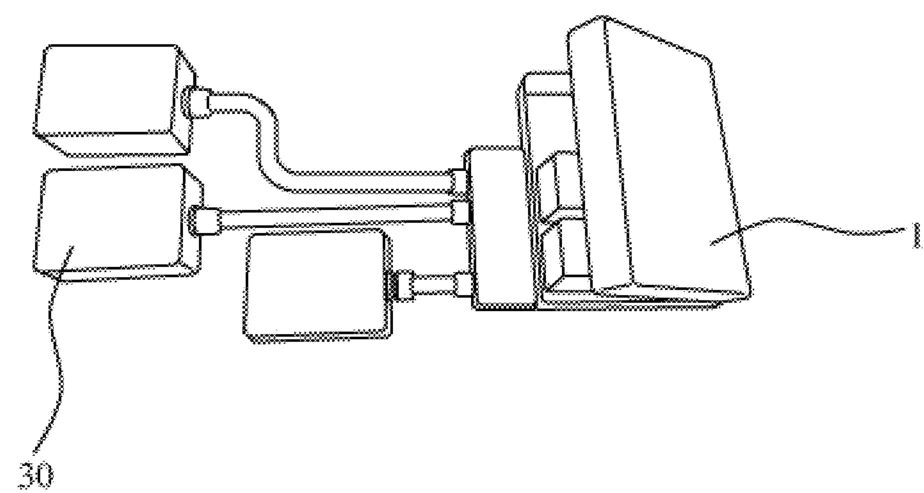
FIG. 7 is a photo showing an air suction-type detector and a multiple sensing unit according to an embodiment of the present disclosure.
Figure 8:
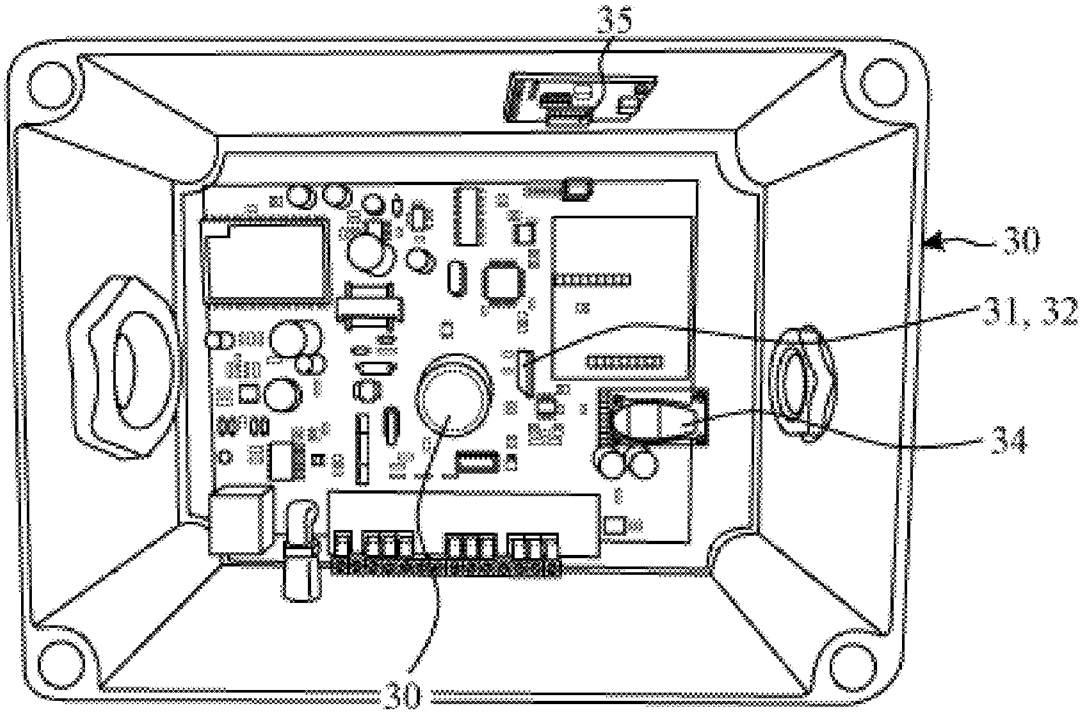
FIG. 8 is a photo showing the inside of a multiple sensing unit according to an embodiment of the present disclosure.

FIG. 6 is a photo showing a battery module connected with a suction hole inside ESS. FIG. 7 is a photo showing an air suction-type detector and a multiple sensing unit according to an embodiment of the present disclosure. FIG. 8 is a photo showing the inside of a multiple sensing unit according to an embodiment of the present disclosure.

An air suction-type detector includes a temperature measurement portion 3 that measures a temperature of a gas introduced into the air suction-type detector; a pressure measurement portion 4 that measures a pressure; a flow rate measurement portion 5 that measures a flow rate in real time; a smoke detection portion 6 that measures a smoke concentration in real time; and a communication portion 7 that transmits the measured values to a monitoring unit to be described hereinafter.

Thus, it is capable of monitoring circumstances of an event and environment change by monitoring and controlling changes in the temperature, pressure, flow rate of an air current introduced through the suction line 20 of the air suction-type detector 1.

In addition, the multiple sensing unit 30 includes a temperature sensor 31 that measures a temperature the gas introduced through the suction line 20 in real time; a humidity sensor 32 that measures a humidity in real time; and a gas sensor that measures a concentration the gas generated in the battery module in real time.

In particular, the gas sensor according to an embodiment of the present disclosure includes a CO sensor 33 that measures CO concentration in real time; a $CO_2$ sensor 34 that measures $CO_2$ concentration in real time; and VOCs sensor 35 that measures VOCs concentration in real time. The gas sensor further includes a transmission portion 36 that transmits these measured values to the monitoring unit 50.

The monitoring unit 50 receives the values for temperature, humidity, $CO_2$ concentration, CO concentration and VOCs concentration, measured in the multiple sensing unit from a receiving portion 51 and then primarily monitors a sign of thermal runaway of the battery. Further, this secondarily monitors the occurrence of fire or thermal runaway based on the smoke concentration measured in the air suction-type detector 1.

The monitoring unit 50 includes database (DB) 52 where preset values for temperature, CO concentration, $CO_2$ concentration and VOCs concentration are stored.

Thus, a determination portion 53 determines a pre-thermal runaway state when any of the values measured in the temperature sensor 31, the CO sensor 33, the $CO_2$ sensor 34 and the VOCs sensor 35 exceeds the respective preset values for temperature, CO concentration, $CO_2$ concentration and VOCs concentration.

Further, the preset smoke concentration value is also stored in the database 52. When a pre-thermal runaway state is identified in the determination portion 53, the determination portion 53, the determination portion 53 determines a fire outbreak stage when the smoke concentration measured in the air suction-type detector 1 exceeds the preset smoke concentration.

Alternatively, the database 52 may store a simulation of when a battery thermal runaway occurs, or graphs showing changes in temperature, CO concentration, $CO_2$ concentration, VOCs concentration and smoke concentration.

The determination portion 53 compares the temperature change graph stored in the database 52 and a temperature change graph measured in the multiple sensing unit 30 in real time. Further, this compares the CO concentration change graph stored in the database 52 and a CO concentration change graph measured in the multiple sensing unit 30. Similarly, each of the graphs showing changes in $CO_2$ concentration and VOCs concentration stored in the database 52 is compared to the respective graphs showing changes in $CO_2$ concentration and VOCs concentration measured in the multiple sensing unit, whereby the signs of thermal runaway are monitored to determine a state of pre-thermal runaway or thermal runaway specifically.

Further, the determination portion 53 matches the smoke concentration graph stored in the database 52 with the smoke concentration change graph measured in the air suction-type detector 1, in order to determine whether thermal runaway and fire have occurred and to identify a state of fire.

In addition, the monitoring unit 50 may display the graphs showing changes in temperature, CO concentration, $CO_2$ concentration and smoke concentration in real time.

Further, the system includes an alarm unit 54, which may transmit determined data about the identified state of pre-thermal runaway, thermal runaway or fire through audible warnings such as voice and alarm sounds when the determination portion 53 identifies such states.

The system further includes a communication module that transmit such determined data to a preset user terminal 60 belonging to an operator, enabling rapid identification and notification of the identified states.

Further, the configuration and method of the embodiments as described above are not restrictively applied to the aforementioned apparatus and method. The whole or part of the respective embodiments may be selectively combined so as to make various modifications of the embodiments.

FIGURE REFERENCE NUMBERS

1: an air suction-type detector (ADS)
2: an ESS
3: a temperature measurement portion
4: a pressure measurement portion
5: a flow rate measurement portion
6: a smoke detection portion
7: a communication portion
10: a battery module
20: a suction line
21: a suction hole
22: a suction pump
30: a multiple sensing unit
31: a temperature sensor
32: a humidity sensor
33: a CO sensor
34: $CO_2$ sensor
35: a VOCs sensor
36: a transmission portion
50: a monitoring unit
51: a receiving portion
52: DB
53: a determination portion
54: an alarm unit
55: a display portion
60: a user terminal
100: an early fire detection system for an ESS battery module

The invention claimed is:

1. An early fire detection system for an energy storage system (ESS) battery module, comprising:
an air suction detector that is fitted to an exterior of the ESS battery module and detects fire by introducing gas inside the ESS battery module;
a suction line, of which one end is connected to the ESS battery module, sucking gas inside the ESS battery module in real time and introducing the gas into the air suction detector;
a suction pump that is fitted to one side of the suction line and supplies power for drawing air from inside the ESS battery module into the suction line;
a multiple sensing unit that is fitted to one side of the suction line and senses a temperature of the gas introduced through the suction line, as well as any generated gas, the multiple sensing unit comprising:
a temperature sensor that measures a temperature of gas introduced through the suction line, in real time;
a humidity sensor that measures a humidity in real time; and
a gas sensor that measures a concentration of the generated gas which is generated during thermal runaway, the gas sensor comprising a CO sensor, a $CO_2$ sensor and a VOCs sensor, and
a monitoring unit that receives measurements of concentration, temperature and humidity of the generated gas from the multiple sensing unit, primarily monitoring battery thermal runaway and secondarily monitoring a fire outbreak based on a smoke concentration measured in the air suction detector.

2. The early fire detection system of claim 1,
the monitoring unit further comprising:
a database that stores preset values for temperature, CO concentration, $CO_2$ concentration and VOCs concentration; and
a determination portion that determines a state when each value measured in the temperature sensor, the CO sensor, the $CO_2$ sensor and the VOCs sensor, respectively exceeds the respective preset values for temperature, CO concentration, $CO_2$ concentration and VOCs concentration as a sign of thermal runaway.

3. The early fire detection system for an ESS battery module of claim 2, wherein a preset smoke concentration value is stored in the database,
the determination portion determines a fire outbreak stage when a pre-thermal runaway state is identified and the smoke concentration measured in the air suction detector exceeds the preset smoke concentration value.

4. The early fire detection system for an ESS battery module of claim 3, wherein
the database stores a simulation of when the battery thermal runaway occurs, or a temperature change graph, a CO concentration change graph, a $CO_2$ concentration change graph, a VOCs concentration change graph and a smoke concentration graph.

5. The early fire detection system for an ESS battery module of claim 4, wherein
the determination portion determines the pre-thermal runaway state or a thermal runaway state by performing at least one of:
matching the temperature change graph stored in the database with a temperature change graph measured in the multiple sensing unit;

matching the CO concentration change graph stored in the database with a CO concentration change graph measured in the multiple sensing unit;

matching the $CO_2$ concentration change graph stored in the database with a $CO_2$ concentration change graph measured in the multiple sensing unit; or matching the VOCs concentration change graph stored in the database with a VOCs concentration change graph measured in the multiple sensing unit.

6. The early fire detection system for an ESS battery module of claim 5, wherein the determination portion determines whether or not fire has occurred and identifies a state of fire by matching the smoke concentration graph stored in the database with a smoke concentration change graph measured in the air suction detector.

7. The early fire detection system for an ESS battery module of claim 6, the monitoring unit further comprising:

a display portion that displays the measured temperature change graph, CO concentration change graph, $CO_2$ concentration change graph and smoke concentration change graph.

8. The early fire detection system of claim 7, further comprising:

an alarm unit that transmits determination data on when the determination portion determines the pre-thermal runaway state, the thermal runaway state or a state of fire, as alarm data.

9. The ESS battery early fire detection system of claim 8, further comprising:

a communication module that transmits the determination data to a preset user terminal.

* * * * *